United States Patent
Hossack

(10) Patent No.: US 6,517,488 B1
(45) Date of Patent: Feb. 11, 2003

(54) MEDICAL DIAGNOSTIC ULTRASOUND SYSTEM AND METHOD FOR IDENTIFYING CONSTRICTIONS

(75) Inventor: John A. Hossack, Charlottesville, VA (US)

(73) Assignee: Acuson Corporation, Mountain View, CA (US)

(*) Notice: Subject to any disclaimer, the term of this patent is extended or adjusted under 35 U.S.C. 154(b) by 165 days.

(21) Appl. No.: 09/606,515

(22) Filed: Jun. 29, 2000

(51) Int. Cl.⁷ .................................................. A61B 8/06
(52) U.S. Cl. ...................................... 600/454; 128/916
(58) Field of Search ............................... 600/437, 441, 600/443, 450–456; 324/306; 128/916

(56) References Cited

U.S. PATENT DOCUMENTS

| | | | |
|---|---|---|---|
| 4,476,874 A | * 10/1984 | Taenzer et al. ............. | 600/441 |
| 4,559,952 A | * 12/1985 | Angelsen et al. ........... | 600/455 |
| 5,058,594 A | * 10/1991 | Lazenby ...................... | 600/454 |
| 5,341,808 A | * 8/1994 | Rickey et al. .............. | 600/437 |
| 5,417,214 A | * 5/1995 | Roberts et al. ............. | 324/306 |
| 5,471,990 A | * 12/1995 | Thirsk ......................... | 600/455 |
| 5,474,073 A | 12/1995 | Schwartz et al. | |
| 5,623,930 A | 4/1997 | Wright et al. | |
| 5,682,896 A | * 11/1997 | Scheib et al. .............. | 600/456 |
| 5,771,896 A | 6/1998 | Sliwa, Jr. et al. | |
| 5,876,345 A | 3/1999 | Eaton et al. | |
| 5,928,151 A | 7/1999 | Hossack et al. | |
| 5,967,987 A | 10/1999 | Sumanaweera et al. | |
| 5,997,480 A | * 12/1999 | Sumanaweera et al. ..... | 600/454 |
| 6,014,473 A | 1/2000 | Hossack et al. | |
| 6,045,508 A | 4/2000 | Hossack et al. | |
| 6,095,976 A | * 8/2000 | Nachtomy et al. .......... | 600/443 |
| 6,193,665 B1 | * 2/2001 | Hall et al. .................. | 600/455 |
| 6,261,233 B1 | * 7/2001 | Kantorovich ............... | 600/454 |

OTHER PUBLICATIONS

Paik et al., "Automated Flight Path Planning for Virtual Ends" Medical Physics, May, 1998; 25(5): 629–637.

Scott Unbaugh, "Computer Vision and Image Processing—A Practical Approach . . . ", Prentice Hall PTR, Upper Saddle River, NJ 07458.

Carlo Palombo, M.D. et al., "Ultrafast Three–Dimensional Ultrasound Application to Carotid Artery Imaging", 1998; pp. 1631–1637.

* cited by examiner

Primary Examiner—Marvin M. Lateef
Assistant Examiner—Ali M. Imam

(57) ABSTRACT

A method and system for identifying constrictions in a vessel are provided. Total blood volume flow is measured at various locations along the vessel. The total volume flow must be conserved. Regions with a different volume flow than expected (e.g. areas associated with a lower volume that violates conservation of flow) are identified as suspicious. Suspicious regions are likely associated with dropout artifact. Actual constrictions are determined from the geometry of images where the region is not suspicious.

27 Claims, 2 Drawing Sheets

MEDICAL DIAGNOSTIC ULTRASOUND SYSTEM AND METHOD FOR IDENTIFYING CONSTRICTIONS

BACKGROUND

This invention relates to a medical diagnostic ultrasound system and method for identifying constrictions. In particular, regions of little or no flow in a vessel due to constrictions of the vessel are distinguished from artifact signal dropout that wrongly suggests little or no flow.

Accurate diagnosis of constrictions in blood vessels, such as the carotid, assists medical treatment. Three-dimensional ultrasound images of the carotid are rendered from blood flow information. The rendered images show arterial constrictions in the carotid. The geometry of the rendering is examined for any constriction. Since imaging artifact signals may also result in an apparent constriction where no or a smaller constriction exists, human judgement is required to determine whether the shown constriction is attributable to an actual constriction or signal artifact. This subjective technique is prone to error.

BRIEF SUMMARY

The present invention is defined by the following claims, and nothing in this section should be taken as a limitation on those claims. By way of introduction, the preferred embodiment described below includes a method and system for identifying constrictions in a vessel. Total blood volume flow is measured at various points along the vessel. The total volume flow is conserved. Regions with a different volume flow than expected (e.g. areas associated with a lower volume that violates the conservation of flow principle) are identified as suspicious. Suspicious regions are likely associated with a dropout artifact. Actual constrictions are determined from the geometry of images where the region is not suspicious.

In one aspect, a medical diagnostic ultrasound method for identifying a constriction in a vessel with an ultrasound system is provided. Volume fluid flow within the vessel is measured. An image of a portion of the vessel is generated.

An artifact is indicated in the image in response to the volume fluid flow measurement. In another aspect, a constriction in the image is indicated as a function of the volume fluid flow measurement.

Further aspects and advantages of the invention are discussed below in conjunction with the preferred embodiments.

DETAILED DESCRIPTION OF THE PREFERRED EMBODIMENTS

According to fluid dynamics, the volume flow at one location along an enclosed vessel is the same at other locations along the same enclosed vessel. Where the enclosed structure constricts, the volume flow is the same as at wider portions. In contrast with the artifact case, the velocity increases to maintain constant total volume flow. For vessels with actual constrictions, the total volume flow at the constriction is substantially the same as at other locations along the vessel. If an image shows a constriction but the volume flow is different than at other locations, the apparent constriction is likely due to a dropout artifact.

Ultrasound systems are capable of measuring volume flow in a vessel. Based on these measurements, regions of an image associated with different volume flow are highlighted. Where a constriction appears in the image but is highlighted, an artifact is indicated. Where a constriction appears in the image and is not highlighted, an actual constriction is indicated. Alternatively, the regions associated with expected volume flow are highlighted.

I. SYSTEM FOR INDICATING CONSTRICTIONS

Various ultrasound systems are capable of calculating the flow measurement and generating a responsive image. For example, a Sequoia®, Aspen™ or 128XP® ultrasound system manufactured by Acuson Corporation may be used. Other ultrasound systems, such as systems provided by other manufacturers, may be used.

Figure 1:
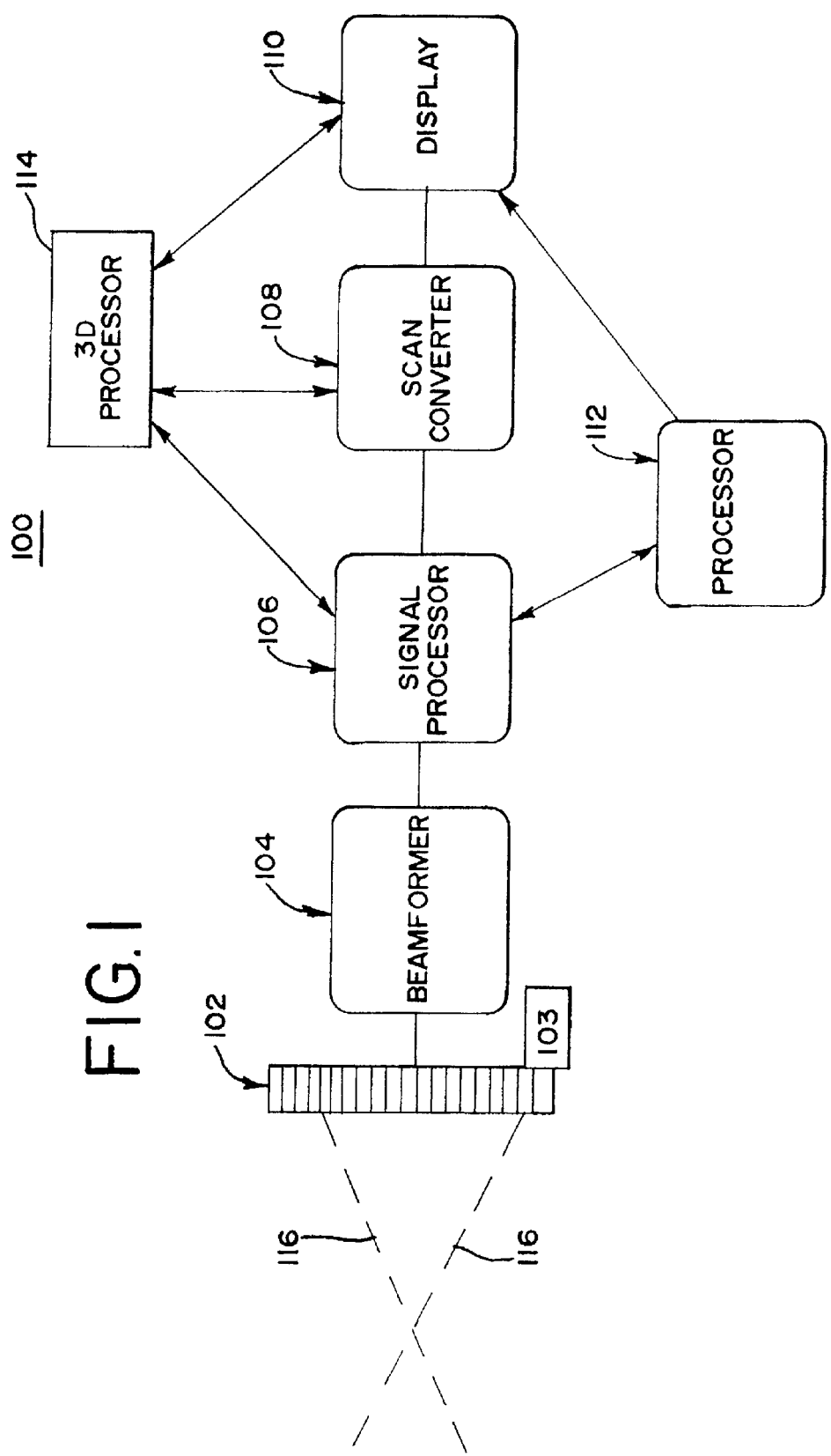
FIG. 1 is a block diagram of one embodiment of a medical diagnostic ultrasound system for identifying a constriction in a vessel.

FIG. 1 shows one embodiment of an ultrasound system for identifying constrictions in a vessel at 100. The system 100 includes a data path comprising a transducer 102, a beamformer 104, a signal processor (estimator) 106, a scan converter 108 and a display device 110. A processor 112 connects to the data path, such as connecting at least to the signal processor 106. A three-dimensional image processor 114 also connects to the data path, such as connecting with one or more of the signal processor 106, the scan converter 108 and the display device 110. In alternative embodiments, the three-dimensional image processor 114 is within the data path, such as being part of the signal processor 106 or scan converter 108, between the signal processor 106 and scan converter 108, or between the scan converter 108 and the display device 110.

The transducer 102 is any of various transducers, such as a linear or curved linear array of piezoelectric elements. In one embodiment, a multi-dimensional transducer is used. For example, multiple image registration, 1.5 or 2 dimensional transducers are used. These transducers include elements arrayed substantially on a plane (i.e. arrayed in two dimensions). For a description of multiple image registration transducers, see U.S. Pat. No. 6,014,473, the disclosure of which is incorporated herein by reference. One multiple image registration transducer embodiment generally includes elements in a plane arrayed in an I pattern. Three scan planes associated with the I pattern may be generated. For T or +beam pattern transducers, two scan planes associated with the T and +patterns, respectively, may be generated. Transducers with other element patterns may be used. For 1.5 or 2 dimensional transducers, any of the various scan plane formats or patterns may be generated.

In one embodiment, the transducer 102 is connected with a catheter or endoscope for insertion into a patient. For example, the transducer 102 is provided on an AcuNav™ Acuson ultrasound imaging catheter or the catheter described in U.S. Pat. No. 5,876,345, the disclosure of which is incorporated herein by reference. Other catheter and transducer devices may be used. As another example, the transducer 102 is provided on one of the endoscopes described in U.S. Pat. Nos. 5,771,896 or 6,045,508, the disclosures of which are incorporated herein by reference. Other endoscope and transducer devices may be used. In alternative embodiments, the transducer 102 comprises a hand held or mounted transducer for use external to the patient.

The beamformer 104 is constructed as known in the art. The beamformer 104 may comprise separate transmit and receive beamformers. The beamformer 104 produces excitation signals for each or a subset (i.e. a sub-aperture) of the elements of the transducer 102. The excitation signals are processed, such as by applying a relative delay and/or amplitude, to focus ultrasonic waveforms along one or more scan lines 116. The scan lines may be at any of various angles relative to the transducer 102 and originate at various locations along the transducer 102. The plane defined by two or more scan lines or any linear combination of transducer elements comprises a scan plane.

The acoustic waveforms are reflected off of structures within a body, including moving fluid within an enclosed structure, as echoes. The echoes are detected by the elements of transducer 102 and provided as voltage signals to the beamformer 104. The beamformer 104 sums the voltage signals and outputs ultrasound data representative of structures along the one or more scan lines.

In one embodiment, the beamformer 104 includes a filter for isolating information in a desired frequency band. For example, a bandpass filter, a highpass filter, a lowpass or combinations thereof selectively pass one or both of data at the transmit or fundamental frequency band or data at a harmonic of the fundamental frequency band. As another example, a demodulator and a filter are provided to isolate information at a desired frequency band.

The signal processor (estimator) 106 comprises a construction known in the art, such as a Doppler digital signal processor or filtering device for providing Doppler estimates from the representative ultrasound data. The signal processor 106 may also include a parallel B-mode processor or spectral Doppler processor. A clutter filter may also be included. The signal processor 106 estimates the Doppler velocity, energy, and/or variance for each of various points or ranges along each scan line. The estimates and any B-mode information may be stored in a memory, such as a CINE™ or image video loop memory.

The estimates, such as Doppler velocity, and/or any B-mode information representing areas in the scan plane or along a scan line are provided to the scan converter 108. The scan converter 108 is a processor or dedicated hardware for formatting the estimates into a Cartesian coordinate system for display.

The display device 110 comprises a monitor, such as a color monitor, flat panel display, television or other device for displaying an image. For two-dimensional imaging, the scan converted ultrasound data representing the scan plane is displayed on the display device 110 as a B-mode intensity, Doppler velocity, Doppler energy, or Doppler variance image. Images that are a combination of two or more of these types of data may also be generated.

The processor 112 is a digital signal processor or multipurpose processor for calculating the volume flow from the Doppler velocity estimates or other data. Alternatively, other hardware, such as an accumulator, summer and buffer, may calculate the volume flow. The processor 112 obtains information, such as Doppler velocities, Doppler energies, Doppler variances, Doppler spectrum parameters, orientation information corresponding to the various scan lines and/or other information for calculating volume flow and generating a image of the vessel as discussed below.

The processor 112 may also provide control instructions to various components of the system 100. For example, the processor 112 controls the beamformer 104 to generate acoustic waveforms along scan lines 116 in certain directions and scan formats and/or controls generating of a three-dimensional representation by the three-dimensional image processor 114. Alternatively, a separate processor provides control of the system 100.

The processor 112 or another processor may also coordinate user input. The user designates a region of interest on a displayed ultrasound image. For example, the region of interest corresponds to pixels associated with the enclosed structure for calculation of volume flow. Alternatively, the region of interest is identified by the system 100 by applying one or more thresholds to the Doppler estimates or B-mode information as discussed below. The identified regions, regardless of the process of identification, are stored in the processor 112, another processor or a memory separate from the processor 112. Alternatively, the user configures the system 100 to scan only the region of interest.

The processor 112 interacts with the three-dimensional image processor 114 to generate a three-dimensional representation that indicates constrictions. The three-dimensional image processor 114 comprises a remote computer. For example, 3D image processor 114 comprises a remote workstation, such as the AEGIS workstation of Acuson Corporation. Alternatively, an on-board computer is used, such as the processor 112 or another processor. For example, see U.S. Pat. No. 6,159,150, the disclosure of which is incorporated herein by reference.

For 3D imaging, a plurality of scans of the vessel are performed. The representation is rendered from data from different scan planes by the three-dimensional image processor 114. The data used comprises data output by the signal processor 106 or the scan converter 108, including Doppler velocity, Doppler energy, Doppler variance, B-mode and combinations thereof.

In one embodiment, the three-dimensional image processor 114 and the system 100 comprise the system described in U.S. Pat. No. 5,928,151, the disclosure of which is incorporated herein by reference. The system 100 operates as described in the above referenced '151 patent for rendering an image using data corresponding to harmonic or fundamental frequencies.

To render a three-dimensional representation, the scan planes for the data are aligned. Many approaches can be taken in aligning the image data frames to provide the desired three-dimensional reconstruction of the data. For example, mechanical or electrical systems determine a position of the transducer 102 relative to the patient for each scan plane (e.g. absolute position sensors as represented by optional sensor 103). This positioning device may be a magnetic sensor such as those available from Ascension Technology, Burlington, VT. Alternatively, the position of the scan planes may be assumed, entered manually or determined electronically from a 2D or 1.5D transducer array. In another alternative, the data may be used to determine the position of the scan plane, such as described in U.S. Pat. No. 6,014,473.

For reconstruction, the 3D image processor 114 uses the image data frames and the position information to generate information for the three dimensional representation of a volume. Information from the two-dimensional image data frames is converted to a 3D grid, such as a regularly (equal) spaced volume grid. Successive image data frames are inserted into their appropriate XYZ locations of the 3D volume as a function of the positional information.

Once all frames have been inserted, intermediate points are calculated using three-dimensional interpolation techniques relying on the eight or other number of closest known data points. For example, data samples in the 3D grid are linearly interpolated from neighboring data samples, such as 4 or 8 samples. Other interpolation techniques may be used, such as spline fitting.

Instead of scan planes, spaced line data, such as associated with an ultrasound scan line, is used to interpolate to the 3D grid. These data samples are not yet interpolated to the arbitrary two-dimensional planes by scan conversion. Other approaches to 3D reconstruction may be used, such as a nearest neighbor search. The 3D image processor 114 uses software to construct the 3D representation based on the input information discussed above. Various commercially available software and fixtures are available for 3D reconstruction.

Alternatively, the software for reconstruction of the 3D representation is written specifically for the system 100 described above.

Various visualization software, such as Fortner Research LLC's T3D, and techniques may be used to present the 3D image or reconstruction on a two-dimensional display. Cross sections can be taken in various planes, including a wide variety of planes selected by the user that do not correspond to the scan planes of the image data. The selected planes are interpolated from the 3D grid data samples. For 3D imaging, the 3D representation on the display 38 may be rotated, zoomed and viewed in perspective as is well known in the art.

Various techniques for 3D imaging are possible, such as surface renderings and volume rendering displays. Volume rendering comprise alpha bending, maximum intensity projection or minimum intensity projection. As an alternative to the surface rendering discussed above, the polygon mesh is derived by applying border detection to each image plane (two-dimensional representation). A polygon mesh is formed by logically linking the detected borders

II. CONSTRICTION INDICATION

Figure 2:
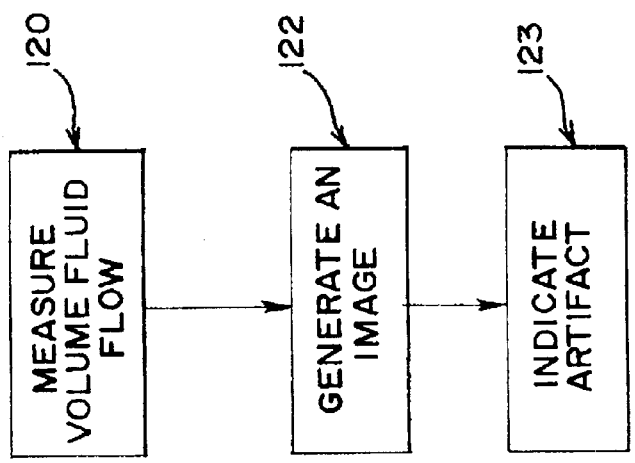
FIG. 2 is a flow chart of one embodiment of a method to identify a constriction.

The 3D representation image or a 2D image is displayed to identify any artifact or actual constriction as a function of the volume flow information measured by the system 100. FIG. 2 is a flow chart representing acts for indicating artifacts and actual constrictions using the system 100.

In act 120, the volume flow of fluid in the vessel is measured. An image, such as a 3D representation, is generated in act 122. In act 124, an artifact or constriction is indicated as a function of the volume fluid flow.

Figure 3:
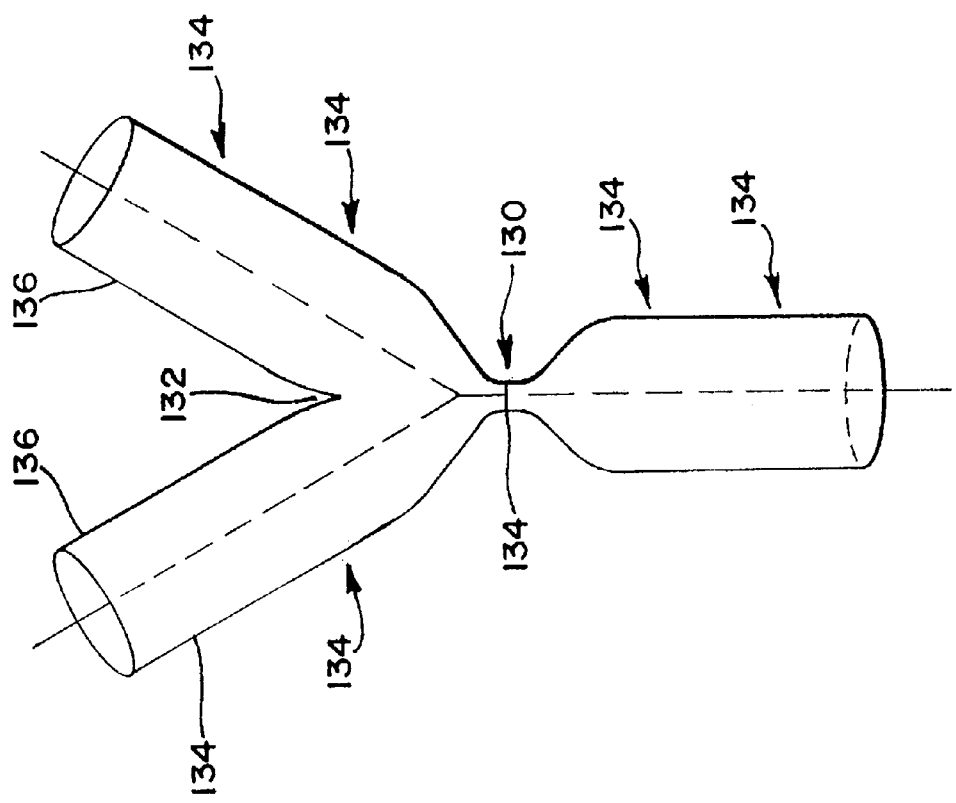
FIG. 3 is a graphical representation of one embodiment of a vessel with a constriction.

The volume fluid flow is measured at a plurality of locations along the vessel. FIG. 3 shows a graphical representation of one embodiment of a carotid vessel. A constriction 130 in shown adjacent to a bifurcation 132. Volume fluid flow is measured at locations downstream and upstream of the constriction 130, such as shown as measurement regions 134. Where one or more bifurcations 132 exist, the volume fluid flow in each branch 136 is measured. The volume fluid flow for all branches 136 corresponding to the same flow is summed to determine a total volume fluid flow (i.e. the volume fluid flow is calculated for each of all downstream and upstream branches 136 subject to the same volume flow from the heart). The flow feeding an upstream portion of the carotid is the same as the sum of the flow feeding downstream branches 136. The regions 134 are determined automatically by the system 100, such as at regular intervals, or in response to user input.

The volume fluid flow is measured as a function of Doppler velocity data. Preferably, aliasing of the Doppler velocity data is avoided, such as by automatically or manually increasing the range of velocities. A lack of aliasing may be shown by a lack of color "wrap around" (i.e. no flow away from the transducer in the middle of imaged flow showing flow towards the transducer). The Doppler velocity data is obtained from the signal processor 106, the scan converter 108 or another source. Where the Doppler velocity data comprises image pixel or color data, the detected Doppler velocities are decoded using a color table. For example, see U.S. Pat. No. 6,190,321, the disclosure of which is incorporated herein by reference. Other types of data may be used for measuring volume fluid flow.

In one embodiment, the Doppler velocity data is corrected as a function of an angle of flow. The user indicates a direction of flow associated with each location 134 for calculating volume fluid flow. The Doppler velocity values are increased as a function of the angle of flow relative to the transducer 102. Alternatively, angle correction is performed automatically by the system 100 either for all Doppler velocity values or for values corresponding to user indicated or system determined measurement locations 134. For example, automatic angle correction is shown in U.S. Pat. No. 5,679,078, the disclosure of which is incorporated herein by reference. Angle correction may also be automatically determined as disclosed in U.S. Pat. Nos. 5,967,987 or 6,293,914, the disclosures of which are incorporated herein by reference. In alternative embodiments, the Doppler velocity data is not angle corrected. This alternative is particularly effective where the angle of flow is substantially the same along the entire length of the vessel portion of interest, such as where linear scans of vessels largely parallel to the skin surface (e.g. carotid) are used.

For each measurement region 134, a cross-section of the vessel is selected. Preferably, the cross-section is perpendicular to the direction of flow. The cross-section is selected automatically as a function of a threshold and system determined angle of flow, in response to user entry of the measurement region and angle of flow, or in response to user indication of a cross-section plane (e.g. region of interest). In one embodiment, the cross-section is selected to be within a scan plane. Alternatively, data for the cross-section is derived from a 3D data set or extrapolated from data for a scan plane.

The volume fluid flow for each measurement region 134 is calculated from the Doppler velocity data for the associated cross-section. The vessel is identified as a function of the Doppler velocity data. Locations associated with a non-zero Doppler velocity indicate the location of the vessel. A threshold may be applied to the Doppler velocity data to further isolate data associated with the vessel. The threshold comprises a Doppler velocity threshold. In alternative embodiments, the threshold is compared to B-mode, Doppler energy or Doppler variance or any combination thereof data associated with a same spatial location.

Where the cross-section includes a plurality of vessels, vessels that are subject to the same flow are selected as a group or individually. If selected individually, volume flow is measured for each vessel and the result is summed.

In one embodiment, the volume flow is determined by integrating all the Doppler velocity values within the vessel in the cross-section. As discussed above, the integrated Doppler velocity values may be selected as a function of a threshold. Where volume fluid flow for two or more branches 134 associated with a same flow point in the vessel system is determined separately, the two or more fluid flow values are summed to determine a total volume flow.

Other measurements for volume flow may be used. For example, the system and method disclosed in U.S. Pat. No. 5,967,987 is used. The volume flow measurements are based on the three-dimensional orientation of the vessel in relation to the transducer 102. Ultrasound information associated with non-colinear scan lines in the same scan plane is obtained for two or more scan planes. The ultrasound information is used to measure average velocities and areas of an enclosed structure. Based on the trigonometric relationship of the vessel orientation to the scan plane, a relationship between the measured average velocities, and the measured areas is established. The volume flow is calculated from the relationship using a least squares error analysis. For this method, manual entry of an angle of flow is not required.

As another example, the system and method disclosed in U.S. Pat. No. 6,293,914 is used. The volume flow measurements are based on the three-dimensional orientation of the vessel in relation to a transducer 102. Velocities associated with two scan lines at different angles in a first scan plane are obtained. A first moment (a parameter) of a Doppler spectrum associated with uniform insonification in a second scan plane are also obtained. The first scan plane is oriented to maximize the displayed area of the enclosed structure in the longitudinal view, and the second scan plane is oriented to minimize the width of the displayed area of the enclosed structure in the lateral view (the first scan plane is substantially perpendicular to the second scan plane). An angle of flow in the enclosed structure is determined as a function of the velocities. Volume flow is determined from the angle of flow and the parameter associated with the second scan plane.

In yet another example, the method and system disclosed in U.S. Pat. No. 5,623,930, the disclosure of which is incorporated herein by reference, is used. Blood flow velocity is measured at a number of locations substantially across the blood vessel (e.g. in a cross-section of the vessel) to obtain an average velocity. Angular dependence of the velocity information is eliminated or reduced by taking multiple measurements with scan planes at different angles or 3D data associated with different angles to the blood vessel. A least squares or other technique is used to determine the volume flow as a function of the multiple measurements. Other volume flow methods and systems may be used, such as the methods disclosed in the backgrounds of the patents cited above.

For cyclical flow, such as in the carotid, the volume flow measurements and/or the data used for generating an image are phased to the cycle. For a cardiac cycle, an EKG trigger device triggers each scan so that data is acquired from a same phase of the cardiac cycle. As an alternative to the EKG device, data acquisition is phased in response to a cycle determined from Doppler data, such as phasing in response to a Doppler velocity cycle. For example, U.S. Pat. No. 6,190,321 discloses determining a phase of the cardiac cycle from color Doppler values extracted from a dual mode image.

In act 122, an image is generated as discussed above. The image comprises one or both of a two-dimensional image or a three-dimensional representation. The image is generated from the same or different data as used for measuring volume flow. For example, a different type of data is used, such as Doppler energy or B-mode data. As another example, data from a different scan is used, such as data obtained before or after the data used to calculate volume flow.

The image represents the vessel. One or more regions of the vessel shown in the image may show an apparent constriction in the vessel. The apparent constriction comprises a narrowing of the vessel. The geometrical information showing an apparent constriction is responsive to either an actual constriction or an artifact of the scan or the system 100.

The measurements of volume flow distinguishes an actual constriction from an artifact. The volume fluid flow is determined at the plurality of locations 134. Fluid dynamics holds that the volume fluid flow at a point downstream is the same as at a point upstream in the vessel. Where volume fluid flow is different, the data may be due to an artifact. An average, median or sample volume fluid flow is determined from the measurements. If the volume fluid flow at a measurement region 134 is different, such as lower, an artifact is possible. Where the volume fluid flow is substantially the same, the data is likely accurate. A threshold amount of difference is determined experimentally to distinguish regions associated with an artifact from other regions.

In one embodiment, regions associated with an artifact are highlighted on the image. For example, pixels representing a certain radius or other shaped region designation around the measurement region 134 are changed in intensity or hue. Highlighting indicates regions associated with an artifact and likewise indicates regions associated with accurate data or an actual constriction. Alternatively, the artifact is indicated by highlighting regions associated with measurement regions 134 corresponding to substantially similar volume fluid flow (e.g. any image regions associated with an artifact are not changed, but other areas are highlighted).

Based on the altered image or in response to a generated command on the display 110, the user is instructed to re-scan the patient in response to detection of a possible artifact. A further instruction may be provided to prompt modification by the user of an imaging parameter, such as prompting modification of a Doppler filter selection or setting, gain, velocity scale or other parameters. Alternatively, the user uses the current scan and considers the indicated possible artifact information in diagnosis.

Since fluids in many vessels change as a function of time in response to the cardiac cycle, images associated with the vessel for each of a plurality of phases of the cardiac cycle may be obtained. A chamber or other object may be visualized as described above, such as a surface rendering, as a function of time. For example, the 3D representation is displayed as a series of images within a heart cycle. This dynamic 3D representation indicates changes in shape and volume over time.

As used in this application, the term "vessel" includes any enclosed region or zone in a body that permits fluid flow therein.

While the invention has been described above by reference to various embodiments, it will be understood that many changes and modifications can be made without departing from the scope of the invention. For example, different types of imaging and volume fluid flow measurement may be used whether now known or later developed.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound method for identifying a constriction in a vessel with an ultrasound system, the method comprising the acts of:
   (a) measuring volume fluid flow within the vessel;
   (b) generating an image of a portion of the vessel; and
   (c) indicating an artifact in the image in response to the volume fluid flow measurement.

2. The method of claim 1 wherein (a) comprises measuring volume fluid flow at a plurality of locations within the vessel.

3. The method of claim 2 wherein (a) comprises measuring volume fluid flow in a downstream portion comprising a plurality of vessel branches and in an upstream portion.

4. The method of claim 2 further comprising:
   (d) determining a region of the vessel associated with a measurement of volume fluid flow that is less than an average volume fluid flow by a threshold amount.

5. The method of claim 1 wherein the measurement of volume fluid flow is responsive to Doppler data, the method further comprising:
   (d) correcting the Doppler data as a function of an angle of flow.

6. The method of claim 1 further comprising:
   (d) performing (a) as a function of the cardiac cycle.

7. The method of claim 1 wherein (a) comprises integrating Doppler values corresponding to a cross section of the vessel for each measurement.

8. The method of claim 1 wherein (b) comprises generating a three dimensional representation of the portion of the vessel.

9. The method of claim 1 wherein (c) comprises highlighting an region of the vessel associated with a different fluid flow than other regions of the vessel.

10. The method of claim 1 further comprising:
    (d) prompting a rescan in response to the indication of (c).

11. A medical diagnostic ultrasound method for identifying a constriction in a vessel with an ultrasound system, the method comprising the acts of:
    (a) measuring volume fluid flow within the vessel;
    (b) generating an image of the vessel; and
    (c) indicating a constriction in the image as a function of the volume fluid flow measurement.

12. The method of claim 11 wherein (a) comprises measuring volume fluid flow at a plurality of locations within the vessel.

13. The method of claim 12 wherein (a) comprises measuring volume fluid flow in a downstream portion comprising a plurality of vessel branches and in an upstream portion.

14. The method of claim 12 further comprising:
    (d) determining a region of the vessel associated with a measurement of volume fluid flow that is less than an average fluid flow by a threshold amount.

15. The method of claim 11 wherein the measurement of volume fluid flow is responsive to Doppler data, the method further comprising:
    (d) correcting the Doppler data as a function of an angle of flow.

16. The method of claim 11 further comprising:
    (d) performing (a) as a function of the cardiac cycle.

17. The method of claim 11 wherein (a) comprises integrating Doppler values corresponding to a cross section of the vessel for each measurement.

18. The method of claim 11 wherein (b) comprises generating a three dimensional representation of the portion of the vessel.

19. The method of claim 11 wherein (c) comprises highlighting an region of the vessel associated with a different volume fluid flow than other regions of the vessel.

20. A medical diagnostic ultrasound system for identifying a constriction in a vessel, the system comprising:
    an ultrasound transducer operable to scan a region comprising a vessel;
    a first processor operable to detect motion in response to data from the transducer;
    a scan converter operable to generate an image of the vessel as a function of the data from the transducer; and
    a second processor operable to calculate volume fluid flow as a function of the detected motion data and operable to determine data associated with an artifact as a function of the volume fluid flow;
    wherein the image indicates a location of the artifact.

21. The system of claim 20 wherein the ultrasound transducer is operable to scan a plurality of regions of the vessel and the second processor is operable to calculate volume fluid flow at a plurality of locations within the vessel.

22. The system of claim 20 wherein the first processor is operable to correct the detected data as a function of an angle of flow.

23. The system of claim 20 further comprising:
    an EKG trigger device, wherein activation of the ultrasound transducer is responsive to the EKG trigger device.

24. The system of claim 20 wherein the second processor is operable to integrate the detected data corresponding to a cross section of the vessel for each calculation of volume fluid flow.

25. The system of claim 20 further comprising:
    a third processor in communication with the scan converter and being operable to generate a three dimensional representation of the portion of the vessel.

26. The system of claim 20 wherein a region of the vessel associated with a different volume fluid flow than other regions of the vessel is highlighted.

27. The system of claim 26 wherein the second processor is operable to determine a region of the vessel associated with a calculation of volume fluid flow that is less than an average volume fluid flow by a threshold amount.

* * * * *